United States Patent
Annett et al.

(10) Patent No.: US 8,905,947 B2
(45) Date of Patent: Dec. 9, 2014

(54) SYSTEM AND METHOD FOR TONGUE FORCE DETECTION AND EXERCISE

(76) Inventors: Mark Annett, Livingston, NJ (US); Eric Friedland, Livingston, NJ (US)

(*) Notice: Subject to any disclaimer, the term of this patent is extended or adjusted under 35 U.S.C. 154(b) by 385 days.

(21) Appl. No.: 13/307,459

(22) Filed: Nov. 30, 2011

(65) Prior Publication Data

US 2012/0143091 A1 Jun. 7, 2012

Related U.S. Application Data

(60) Provisional application No. 61/418,995, filed on Dec. 2, 2010.

(51) Int. Cl.
| | |
|---|---|
| *A61B 5/117* | (2006.01) |
| *A61B 5/103* | (2006.01) |
| *A61B 5/22* | (2006.01) |
| *A61B 5/00* | (2006.01) |

(52) U.S. Cl.
CPC ............... *A61B 5/228* (2013.01); *A61B 5/225* (2013.01); *A61B 5/4542* (2013.01); *A61B 5/7405* (2013.01); *A61B 5/7455* (2013.01); *A61B 2562/0247* (2013.01)
USPC ...................................................... 600/590

(58) Field of Classification Search
USPC ........ 600/587, 590, 364; 178/18.06; 345/174; 73/379.08, 862.044
See application file for complete search history.

(56) References Cited

U.S. PATENT DOCUMENTS

| | | | |
|---|---|---|---|
| 4,585,012 A | 4/1986 | Rumburg | |
| 4,697,601 A | 10/1987 | Durkee et al. | |
| 5,119,831 A | 6/1992 | Robin et al. | |
| 5,609,161 A | 3/1997 | Tura et al. | |
| 5,954,673 A | 9/1999 | Staehlin et al. | |
| 6,050,961 A | 4/2000 | Arnold | |
| 6,190,335 B1 | 2/2001 | Howard et al. | |
| 6,511,441 B1 | 1/2003 | Wakumoto et al. | |
| 6,702,765 B2 | 3/2004 | Robbins et al. | |
| 7,238,145 B2 | 7/2007 | Robbins et al. | |
| 2003/0078521 A1 | 4/2003 | Robbins et al. | |
| 2004/0006263 A1* | 1/2004 | Anderson et al. | 600/364 |
| 2008/0183107 A1 | 7/2008 | Miller et al. | |
| 2010/0184566 A1 | 7/2010 | Munehiro | |
| 2010/0222706 A1 | 9/2010 | Miyahara et al. | |
| 2012/0038583 A1* | 2/2012 | Westhues et al. | 345/174 |

FOREIGN PATENT DOCUMENTS

| | | |
|---|---|---|
| EP | 1 110 501 A1 | 6/2001 |
| JP | 2007 202922 A | 8/2007 |

OTHER PUBLICATIONS

Invitation to Pay Fees/Partial International Search Report issued in PCT/US111062629 on Apr. 10, 2012.

* cited by examiner

*Primary Examiner* — Brian Szmal
(74) *Attorney, Agent, or Firm* — Wolff & Samson PC

(57) ABSTRACT

A force sensing and exercise device for assessment and therapeutic usage is described herein. The force sensing device may include a registration plate, to form a ridge with a body part of a patient and provide a fixed point from which measurements are taken. The force sensing device allows for linear movement as a component of the measurement and the ability to vary exercise resistance continuously over an exercise range. Tactile and auditory feedback is provided to a patient to indicate than an exercise objective has been achieved.

27 Claims, 15 Drawing Sheets

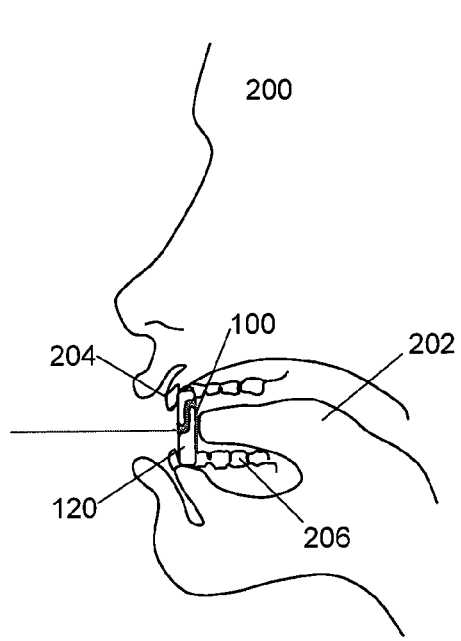
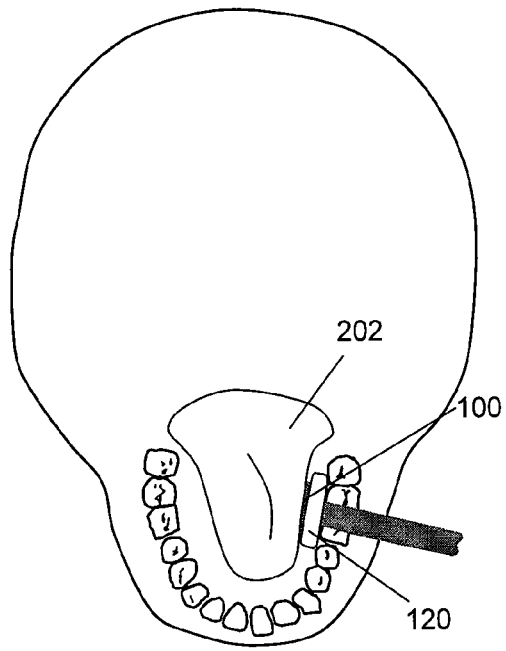
FIG. 2A　　　　　FIG. 2B
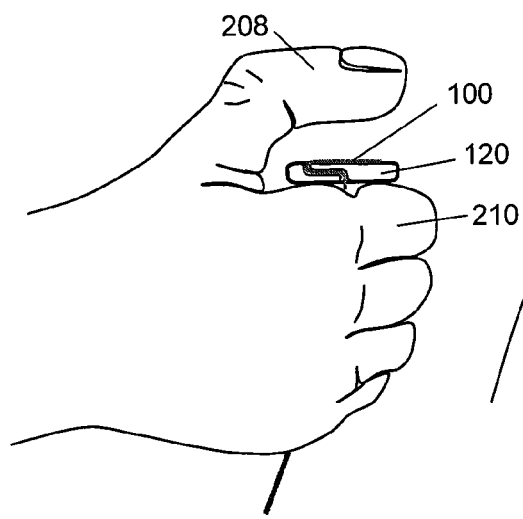
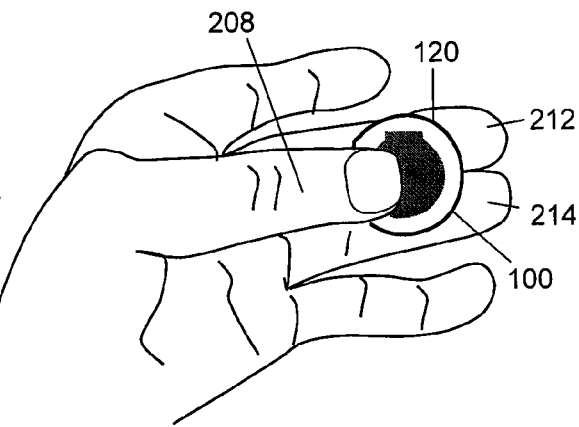
FIG. 2C　　　　　FIG. 2D

SYSTEM AND METHOD FOR TONGUE FORCE DETECTION AND EXERCISE

PRIORITY

This application claims the benefit of U.S. Provisional Application No. 61/418,995, filed Dec. 2, 2010, the entire disclosure of which is incorporated by reference herein.

FIELD

The present application relates to body force measurement, and specifically to tongue force measurement utilized in a medical and/or therapeutic setting.

BACKGROUND

Speech, language, and swallowing difficulties can result from a variety of causes including stroke, brain injury/deterioration, developmental delays/disorders, learning disabilities, cerebral palsy, cleft palate, voice pathology, mental retardation, hearing loss, or emotional problems, and the difficulties can be either congenital, developmental, or acquired.

Speech-language pathologists assess, diagnose, treat, and help to prevent disorders related to speech, language, cognitive-communication, voice, swallowing, and fluency. Treatment modalities may include range of motion and isometric exercises of oral mechanisms. In typical clinical practice, a patient performs isometric exercises against a tongue depressor that is held by a clinician.

As a result, diagnostic baseline data and therapeutic progress is measured by a subjective and qualitative assessment of force against the tongue depressor held by the clinician, or more specifically, the speech pathologist. These types of measurements are inaccurate because the perception of the exerted force against the tongue depressor is inexact and may vary from session to session. Furthermore, patients may be treated by different speech pathologists and thus the overall progress of the patient is subjectively assed by several clinicians.

Although the potential to obtain a reliable measure of tongue strength in multiple directions is described by U.S. Pat. No. 4,697,601 (Durke), devices such as those described by Durke remain too expensive and too cumbersome for clinical use. Durke describes a device using strain gauges to measure tongue force simultaneously in three directions by having an individual push against a tongue cup. A bifurcated tooth plate is fastened to the device, and serves as a means of patient registration (the physical connection between the patient and the fixed point against which measurements are taken). Otherwise, without the bifurcated tooth plate, if the therapist were simply to try and hold the device in place while the patient pushes against it then the therapist influence could easily be as great, or greater, than the effect tying to be measured.

Patient registration is a primary differentiation point between devices designed to measure tongue strength. Early attempts, such as those described by U.S. Pat. No. 4,585,012 (Rumburg), describe table mounted devices where an individual places their chin into a chin rest or a device strapped to a patient's head.

At the other end of the spectrum is the IOWA Oral Performance Instrument described by U.S. Pat. No. 5,119,831 (Robin), which provides no fixed means of patient registration. The clinician simply holds onto a tube placed into the patient's mouth, which has a pressure sensing bulb at its extreme end, that the patient compresses against another body part.

The IOWA Oral Performance Instrument is one of the few devices to be commercially available and has been studied by numerous authors. In clinical practice, it is most often used to measure the pressure an individual can exert against the roof (hard palate) of the patient's mouth. The measurement bulb may also be adhered to a lateral tongue bulb holder. Once adhered, the patient bites down on the holder to create a registration point for side-to-side (lateral) and sticking out the tongue (protrusion) measurements. Therefore, for lateral and protrusion measurements, the patient is required to not only push against the bulb but to simultaneously bite down to keep the device in place, just as would be required by the device described by Durke.

In order to get around the requirement that a patient simultaneously bite and push, U.S. Pat. No. 5,954,973 (Staehlin) and U.S. Pat. No. 6,702,765 (Robbins) both employ a mouth piece that substantially conforms to the patient's anatomy as a means of patient registration. U.S. Pat. No. 6,511,441 (Wakumoto) goes so far as to attach electrodes directly to the patient's hard palate. These customized mouth pieces are expensive to produce and expensive and time consuming for the therapist to employ in daily practice.

Therefore, present devices lack a simple and efficient means of providing patient registration that does not require the patient to simultaneously bite and push.

Unfortunately, a lack of an efficient means of patient registration is not the only deficiency of the devices described above. In almost all the devices, a patient is simply pushing against a "wall" without any sense of movement or work being done. This lack of movement leads to increased patient training needs (especially for those with tongue desensitization), and lack of motivation. It simply is not a fun and enjoyable exercise to repeatedly push against a wall.

Not only is there a lack of a motivational factor in the devices described above, the relevance of simply focusing on peak force (or duration that an individual can maintain 50% of the peak force, referred to as endurance), has been consistently questioned in literature and at clinical conferences.

The Journal of Speech and Hearing Disorders Vol. 52, pages 367-387 November 1987 (Kent) suggests that maximum performance measures may not be relevant to speech because "speaking under ordinary circumstances does not tax the performance capabilities of the speech system." Although it has been more than 20 years since Kent called for a "second generation of speech production measures," the focus of most devices on peak measurement fails to meet the need of providing measurable objective exercise in the range actually utilized in speech production.

In addition, speech production can be effected by repeated use (saying words). However, there is little clinical correlation between real life fatigue and a patient's endurance based upon how long they can push their tongue against a wall. Additional measures are still needed.

U.S. Pat. No. 7,238,145 (Robbins) describes a means of adjusting exercise resistance. However, the adjustment is based on discrete (fixed) settings, rather than continuous (fractional values within a range). Additionally, there is limited feedback indicating exercise completion and difficulty in patient registration.

SUMMARY

A force sensing device is described herein. The force sensing device comprises a force sensing element configured to receive compressive force from a user's tongue. A registration plate, supporting the force sensing element, forms a shelf against a body part to maintain a position of the force sensing element relative to a force exerted by another body part.

In accordance with an embodiment, the registration plate maintains a fixed position from which force measurements are taken.

In accordance with an embodiment, the force sensing device may further comprise a longitudinal element having two ends, a first end coupled perpendicularly to the registration plate.

In accordance with an embodiment, the force sensing device further comprises measurement equipment attached to the force sensing element. The measurement equipment comprises a processor that receives data from the force sensing element, a display that displays the data, and a reset actuator.

In accordance with an embodiment, the force sensing element is a conductive sensor or a pneumatic element.

In accordance with an embodiment, the force sensing device comprises an enclosure that houses the force sensing element, and a cap slidably disposed within the enclosure and engaged to contact with the force sensing element such that the cap pushes against the force sensing element axially in response to the tongue applying compressive force to the cap. A circuit assembly, disposed within the enclosure, may be configured to receive data representative of a sensed compressive force from the force sensing element. A display disposed on the enclosure displays the sensed compressive force based on the data representative of the sensed compressive force received by the circuit assembly.

In accordance with an embodiment, the force sensing device comprises an enclosure that houses the force sensing element, a compressive element within the enclosure, and a cap. The compressive element is coupled to the force sensing element. The cap is slidably disposed within the enclosure and engaged to contact with the compressive element such that the cap pushes against the compressive element axially in response to the tongue applying compressive force to the cap. The cap creates an auditory and tactile indication to a user in response to the cap moving linearly within the enclosure. The force sensing device may further comprise a resistance adjuster, coupled to the compressive element, configured to adjust the compressive element in order to change a resistance of the compressive element.

A method for measuring tongue force is described herein. At least one application of compressive force is received from a user's tongue at a cap that moves slidably relative to an enclosure, against a resistance of a compressive element, in response to receiving an application of compressive force. An auditory and tactile indication is created for the user in response to each instance that an application of compressive force satisfies a resistance threshold. The resistance threshold of the compressive element may be adjusted. The adjustment is performed by setting the resistance threshold based on a predetermined scale associated with a nominal resistance value achievable by a particular population. A scale level of 100 is equivalent to 100 percent of the nominal resistance value. The resistance threshold may be adjusted continuously over a range of interest.

In accordance with an embodiment described herein, a force sensing device may comprise an enclosure, a compressive element within the enclosure, and a cap slidably disposed within the enclosure and engaged to contact with the compressive element such that the cap pushes against the compressive element axially in response to a tongue applying compressive force to the cap.

In accordance with an embodiment described herein, a force sensing device may comprise an enclosure, a force sensing element within the enclosure, and a cap slidably disposed within the enclosure and engaged to contact with the force sensing element such that the cap pushes against the force sensing element in response to a tongue applying compressive force to the cap.

These and other advantages of this disclosure will be apparent to those of ordinary skill in the art by reference to the following detailed description and the accompanying drawings.

BRIEF DESCRIPTION OF THE DRAWINGS

FIGS. 2A, 2B, 2C, and 2D each illustrates an exemplary use of the force sensing device, in accordance with an embodiment of the present disclosure;

DETAILED DESCRIPTION

As discussed in the Background section, there is a need to provide a patient of a pathologist with a more efficient way to exercise their tongue as well as measure tongue force. The system and method described herein, addresses the deficiencies in the art, by providing a system and method for exercise and force measurement.

Figure 1:
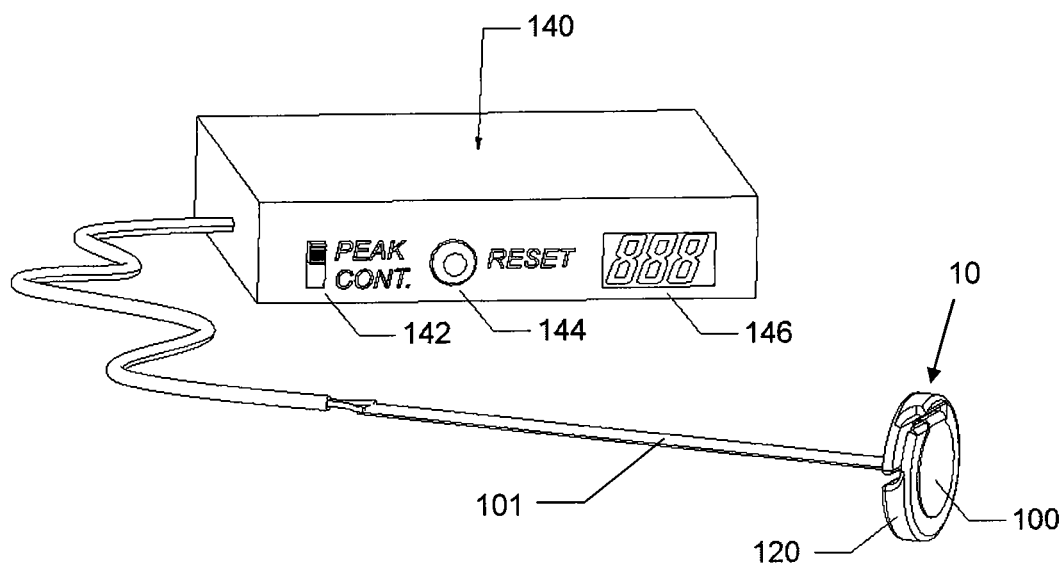
FIG. 1 illustrates an exemplary device for force detection, in accordance with an embodiment of the present disclosure.

FIG. 1 illustrates an exemplary force sensing device, in accordance with an embodiment of the present disclosure. Force sensing device 10 illustrates a force sensing element 100 and a registration plate 120 attached to the force sensing element 100. Additionally shown in FIG. 1, are measurement equipment 140 configured to interface with force sensing device 10 via an interface strip 101.

Force sensing element 100 may be any element or combination of elements including, but not limited to, resistors, force-sensing capacitors; strain gauges, liquid filled bladders with pressure transducers, one-time-use pressure sensitive films and other mechanical means. Force sensing element 100 is configured to receive compressive force from a user's tongue and transmit a conductive force to measurement equipment 140 in order to measure the compressive force of the user's tongue.

Registration plate 120 is shown as a flat circular disk attached to force sensing element 100. However, registration plate 120 may take the form of any other shape deemed most appropriate by a clinician. Registration plate 120 forms a shelf against a first body part and maintains a position of force sensing element 100 relative to a second body part. Once this shelf has been formed, a fixed point from which measurements may be taken is established.

Measurement equipment 140 is configured to receive a signal from force sensing element 100 through interface strip 101. The signal includes data indicating a force measured by force sensing element 100. Measurement equipment 140 includes an operating mode switch 142, a reset switch 144, and a display mechanism 146.

Operating mode switch 142 is operable to switch measurement equipment 140 between at least two different modes. A first mode, "Cont.", is utilized to provide continuous feedback of a level of force measured by force sensing element 100. A second mode, "Peak," is utilized to provide a value of a maximum force measured by force sensing element 100. Operating mode switch 142 may also switch to additional modes related to specific exercise goals for a patient or other measurements related to the level of force measured by force sensing element 100.

Display mechanism 146 may be an LCD display for displaying numeric characters. Display mechanism 146 may also be configured to display alphabetic characters along with graphical images or representations.

Reset switch 144 is configured to reset display mechanism 146 to a zero out a force reading of display mechanism 146. Reset switch 144 may be used, for example, when a new measurement is to be taken.

FIG. 2A illustrates an exemplary use of the force sensing device, in accordance with an embodiment of the present disclosure. In FIG. 2A, the tongue 202 of patient 200 is protruding and pushing against force sensing element 100. Registration plate 120 forms a shelf between an interior surface of patient 200's upper teeth 204 and lower teeth 206.

FIG. 2B illustrates an exemplary use of the force sensing device, in accordance with an embodiment of the present disclosure. In FIG. 2B, tongue 202 is providing a lateral force to force sensing element 100 and registration plate 120, which has been placed at the side of patient 200's mouth.

FIG. 2C illustrates an exemplary use of the force sensing device, in accordance with an embodiment of the present disclosure. In FIG. 2C, force sensing element 100 is in a position to be depressed by thumb 208 of user 200. Registration plate 120 rests upon an index finger 210 of user 200. Force sensing element 100 may be used to measure thumb pinch, as shown in FIG. 2C, where index finger 210 forms a shelf that registration plate 120 rests upon, similar to how registration plate 120 is used to form a shelf with teeth 204 and 206 in FIG. 2A.

FIG. 2D illustrates an exemplary use of force device, in accordance with an embodiment of the present disclosure. In FIG. 2D, force sensing element 100 may measure finger grasp from thumb 208 of user 200. Registration plate 120 forms a shelf with fingers 212 and 214 of user 200.

While the embodiments described thus far are primarily designed for the measurement of body force, alternate uses are possible. For example, force sensing element 100 and registration plate 120 may be connected to a computing device as an input in order to measure sensitivity to touch by pressing force sensing element 100 against a body part and having a patient indicate at what point they feel contact. Additionally, force sensing element 100 may be used as an input to a gaming system.

Figure 3A:
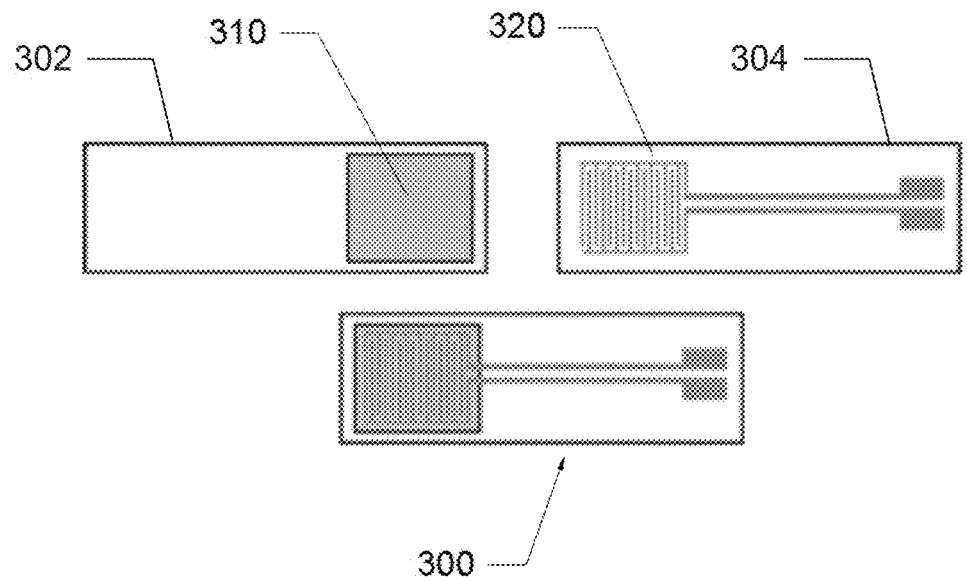
FIGS. 3A and 3B each illustrates a construction of a force sensing resistor, in accordance with an embodiment of the present disclosure.

FIG. 3A illustrates a construction of a force sensing resistor, in accordance with an embodiment of the present disclosure. Specifically, FIG. 3A illustrates a "ShuntMode" construction of a force sensing resistor 300. Force sensing resistor includes two substrate layers of polyester film. A first substrate layer 302 is coated with force-sensing ink 310. A second substrate layer 304 is screen printed with interdigitated conductive electrode fingers 320. First substrate layer 302 and second substrate layer 304 may be positioned facing each other, and may be adhered together using a double sided adhesive, which serves as a spacer around the perimeter of each of the first substrate layer and the second substrate layer to form force sensing resistor 300.

Interdigitated conductive fingers 320 may be screen printed on a substrate such as polyester film with silver or silver/graphite conductive ink, or etched in copper and gold plated on a printed circuit board. Thus, when a force is applied to force sensing resistor 300, the shunt or shorting circuit is complete, thus causing force sensing resistor 300 to sense an applied force. The more force applied, the more conductive the output which may be sent to measurement equipment to measure a value of the applied force.

Figure 3B:
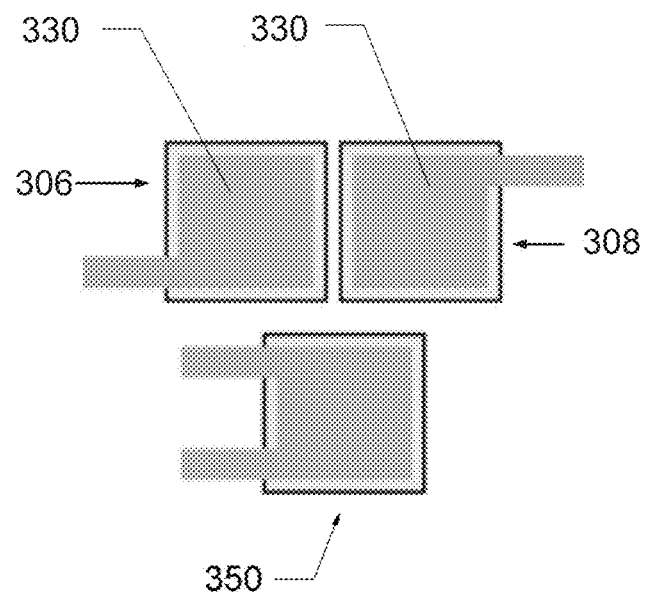

FIG. 3B illustrates a construction of a force sensing resistor, in accordance with an embodiment of the present disclosure. Specifically, FIG. 3B illustrates a "ThruMode" construction of a force sensing resistor 350. Force sensing resistor 350 includes two substrate layers of polyester film. A first substrate layer 306 and a second substrate layer 308 are both coated with force-sensing ink 330. First substrate layer 306 and second substrate layer 308 are positioned facing each other, and an adhesive may be used to laminate the two substrate layers. Operation of force sensing resistor 350 is substantially similar to that of force sensing resistor 300 discussed above.

Figure 4:
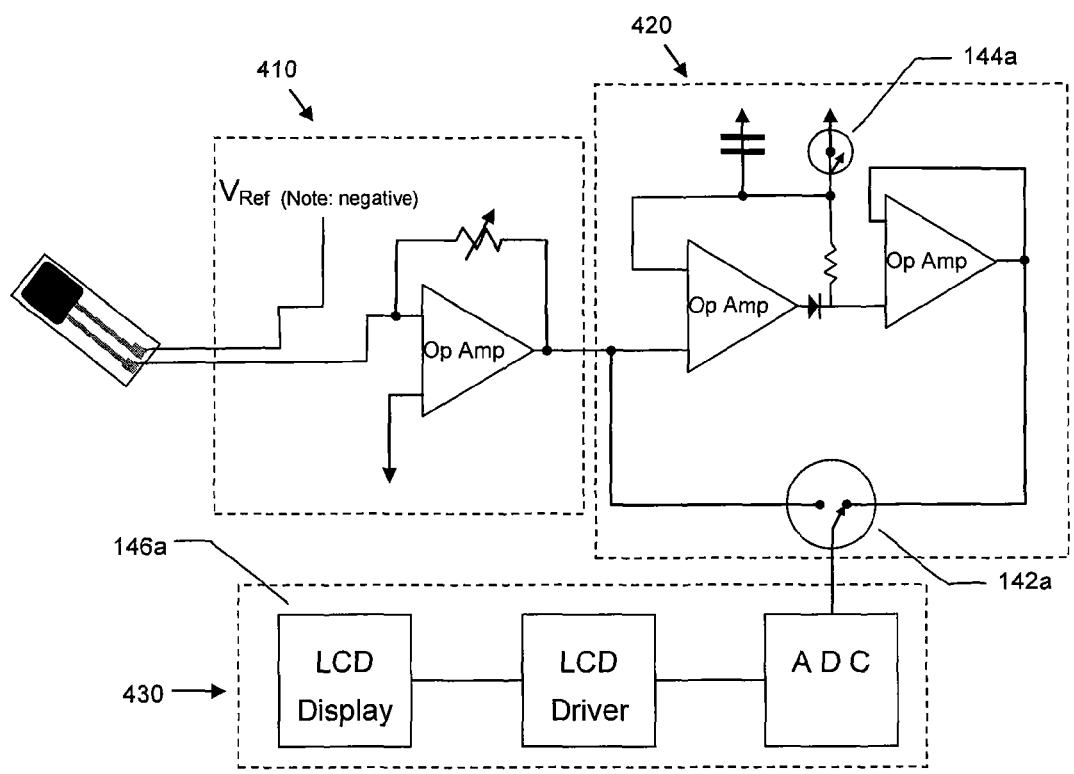
FIG. 4 illustrates a schematic representation of the internal circuitry of the measurement equipment, in accordance with an embodiment of the present disclosure.

FIG. 4 illustrates a schematic representation of the internal circuitry of the measurement equipment, in accordance with an embodiment of the present disclosure. FIG. 4 illustrates internal circuitry, including pre-conditioning circuit 410, peak detection circuit 420, and display circuit 430. More specifically, FIG. 4 also illustrates a schematic representation of display circuit 430, including operating switch 142a, reset switch 144a, and display mechanism 146a, which corresponds to operating switch 142, reset switch 144, and display mechanism 146, respectively, on measurement equipment 140 as shown in FIG. 1. Additionally, but now shown, measurement equipment 140 may include the ability to provide a zero offset voltage as an input to display circuit 430. The internal circuitry may include discrete components, or may be microprocessor or software based via input to a computing device.

Figure 5A:
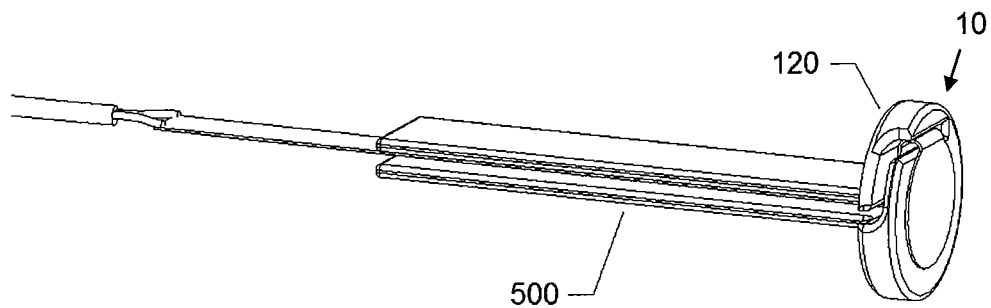
FIG. 5A illustrates an embodiment of a force sensing device including a longitudinal element, in accordance with an embodiment of the present disclosure.

FIG. 5A illustrates a force sensing device including a longitudinal element, in accordance with an embodiment of the present disclosure. Longitudinal element 500, attached to registration plate 120 of force sensing device 10, provides stabilization in the event that a body surface is not available to form a shelf with registration plate 120. Longitudinal element 500 may also, in additional to providing stabilization, serve as a bite or a grip surface.

Figure 5B:
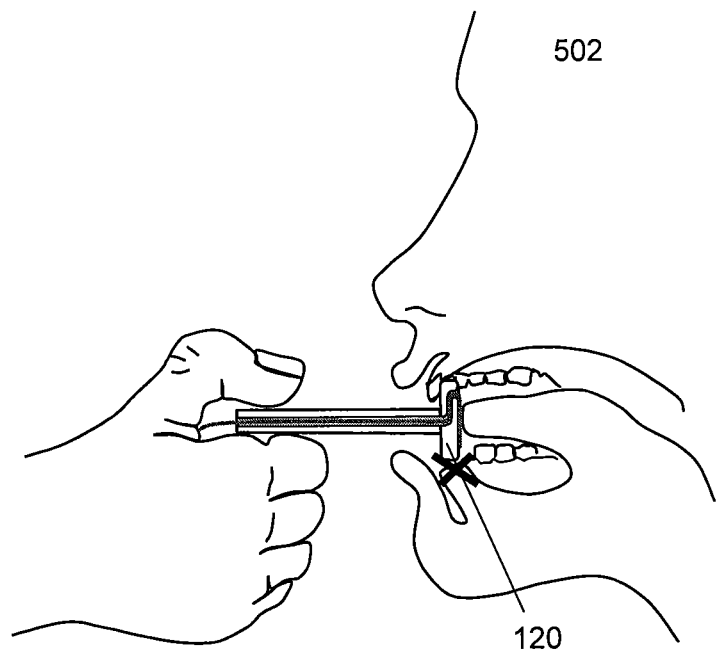
FIG. 5B illustrates usage of a force sensing device with a longitudinal element, in accordance with an embodiment of the present disclosure.

FIG. 5B illustrates usage of a force sensing device with longitudinal element, in accordance with an embodiment of the present disclosure. For example, FIG. 5B shows patient 502, using force sensing device 10 with longitudinal element 500. As patient 502 is missing front bottom teeth, which are necessary to form a shelf with registration plate 120, longitudinal element 500 may be used for stabilization for this particular patient.

Figure 6:
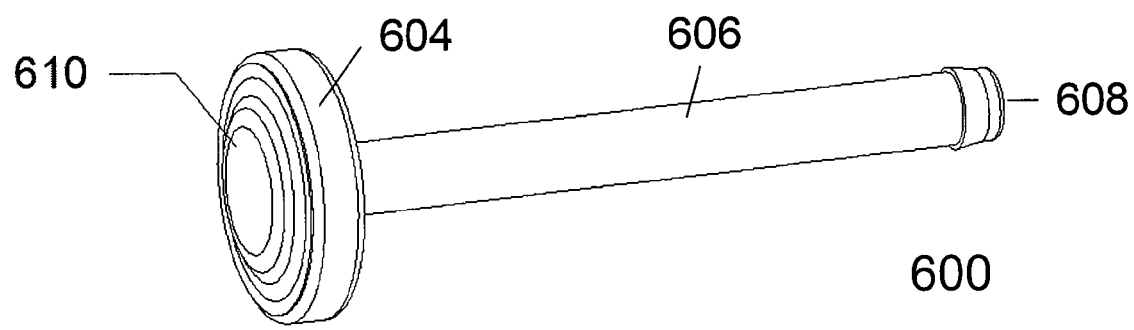
FIG. 6 illustrates a force sensing device including a pneumatic force sensing element, registration plate, and longitudinal element, in accordance with an embodiment of the present disclosure.

FIG. 6 illustrates a force sensing device including a pneumatic force sensing element, registration plate, and longitudinal element, in accordance with an embodiment of the present disclosure. Force sensing device 600 includes pneumatic force sensing element 610, which may be an attached flexible membrane, registration plate 604, and longitudinal element 606. The attached flexible membrane may be attached through use of a peel-and-stick adhesive, solvent bonding, ultrasonic welding, and/or laser welding. A hose (not shown), but connectable to end 608 of longitudinal element 606, may connect force sensing device 600 to a pressure sensor (also not shown) to measure force. Additionally, a second flexible membrane may support a closed fluid filled system.

Figure 7:
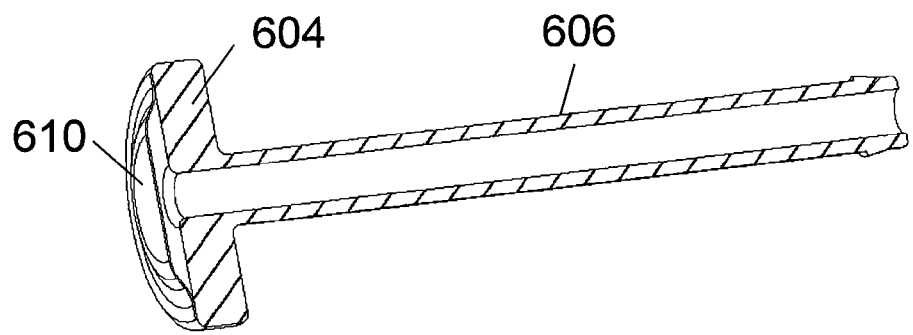
FIG. 7 illustrates a cross-sectional view of the force sensing device shown in FIG. 6, in accordance with an embodiment of the present disclosure.

FIG. 7 illustrates a cross-sectional view of the force sensing device shown in FIG. 6, in accordance with an embodiment of the present disclosure.

Figure 8:
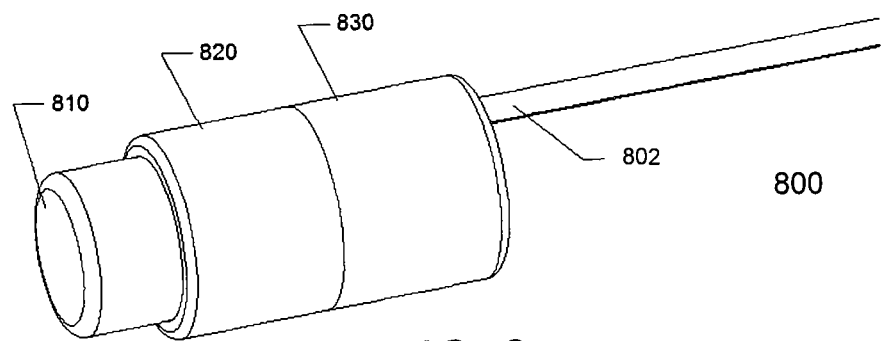
FIG. 8 illustrates a force sensing device without registration plate in accordance with an embodiment of the present disclosure.

FIG. 8 illustrates a force sensing device without registration plate in accordance with an embodiment of the present disclosure. Force sensing device 800 includes a cap 810, barrel 820, and tube 830, connected to force sensing element 802. Cap 810 moves slidably within barrel 820 when cap 810 receives compressive force from a tongue or other body part. This causes a sensor contact to press against force sensing element 802. Further details relating to internal components of barrel 820 and tube 830 are described below.

Figure 9:
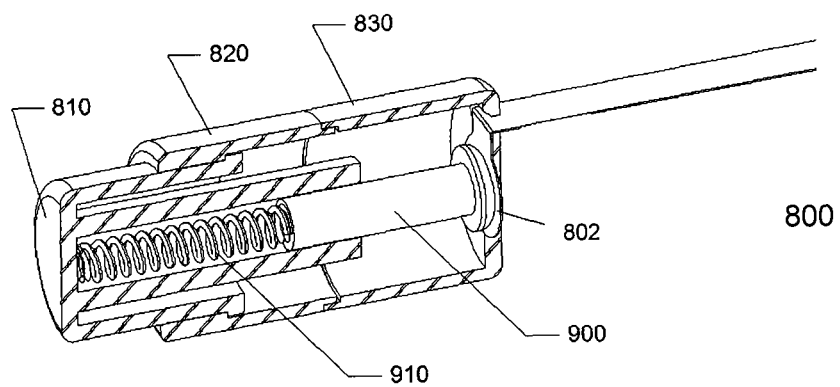
FIG. 9 illustrates a cross sectional view of the force sensing device shown in FIG. 8, in accordance with an embodiment of the present disclosure.

FIG. 9 illustrates a cross sectional view of the force sensing device shown in FIG. 8, in accordance with an embodiment of the present disclosure. This cross sectional view of cap 810, barrel 820, and tube 830 also includes sensor contact 900 and compressive element 910. Sensor contact 900 may be either a rigid or semi-rigid material that optimizes contact with force sensing element 802. As cap 810 receives a compressive force and moves slidably within barrel 820 against a resistance of compression element 910, compression element 910 in turn contacts sensor contact 900, which presses against force sensing element 802. Thus, the compressive force received by cap 810 is transferred to force sensing element 802, which measures the compressive force applied to cap 810 by a patient. A patient is able to experience linear travel as a component of the measurement being taken, rather than simply pushing against a wall.

Figure 10:
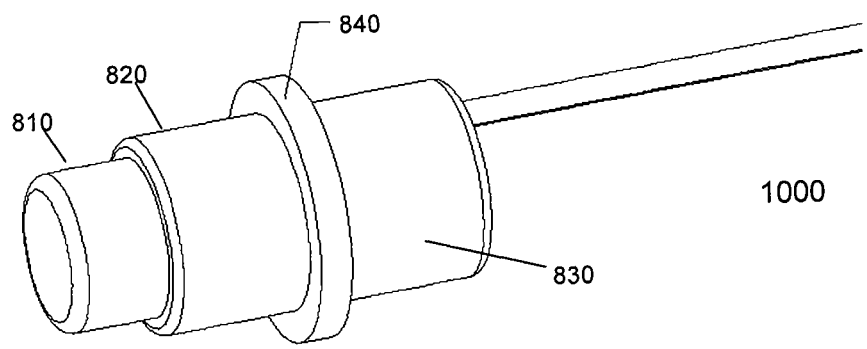
FIG. 10 illustrates the force sensing device shown in FIG. 8, and also including a registration plate, in accordance with an embodiment of the present disclosure.

FIG. 10 illustrates the force sensing device shown in FIG. 8, and also including a registration plate, in accordance with an embodiment of the present disclosure. FIG. 10 illustrates force sensing device 1000, including cap 810, barrel 820, tube 830, registration plate 840, and force sensing element 802. Force sensing device 1000 operates similarly to force sensing device 800 described above. Registration plate 840 provides a shelf between two patient body parts. In FIG. 10, registration plate 840 is placed between barrel 820 and tube 830. However, registration plate 840 may be placed at any position along tongue force detector. For example, to optimize lateral tongue force measurements, registration plate 840 may be positioned at an extreme distal end of barrel 820 on a side where cap 810 slides into barrel 820.

Figure 11:
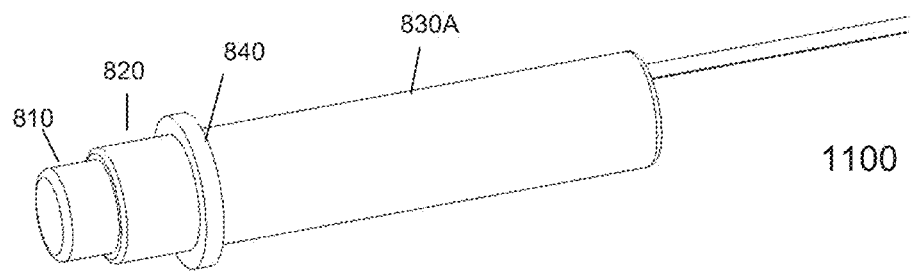
FIG. 11 illustrates the force sensing device shown in FIG. 10, with an extended tube, in accordance with an embodiment of the present disclosure.

FIG. 11 illustrates the force sensing device shown in FIG. 10, with an extended tube, in accordance with an embodiment of the present disclosure. Force sensing device 1100 includes cap 810, barrel 820, tube 830A, registration plate 840, and force sensing element 802. Tongue force detector 1000 operates similarly to tongue force detector 800 described above. The addition of the extended tube 830A provides additional stabilization in the event that a body surface that may be expected for use to form a shelf with registration plate 840 is unavailable. Extended tube 803 may also serve as a bite or grip surface for a patient.

Figure 12:
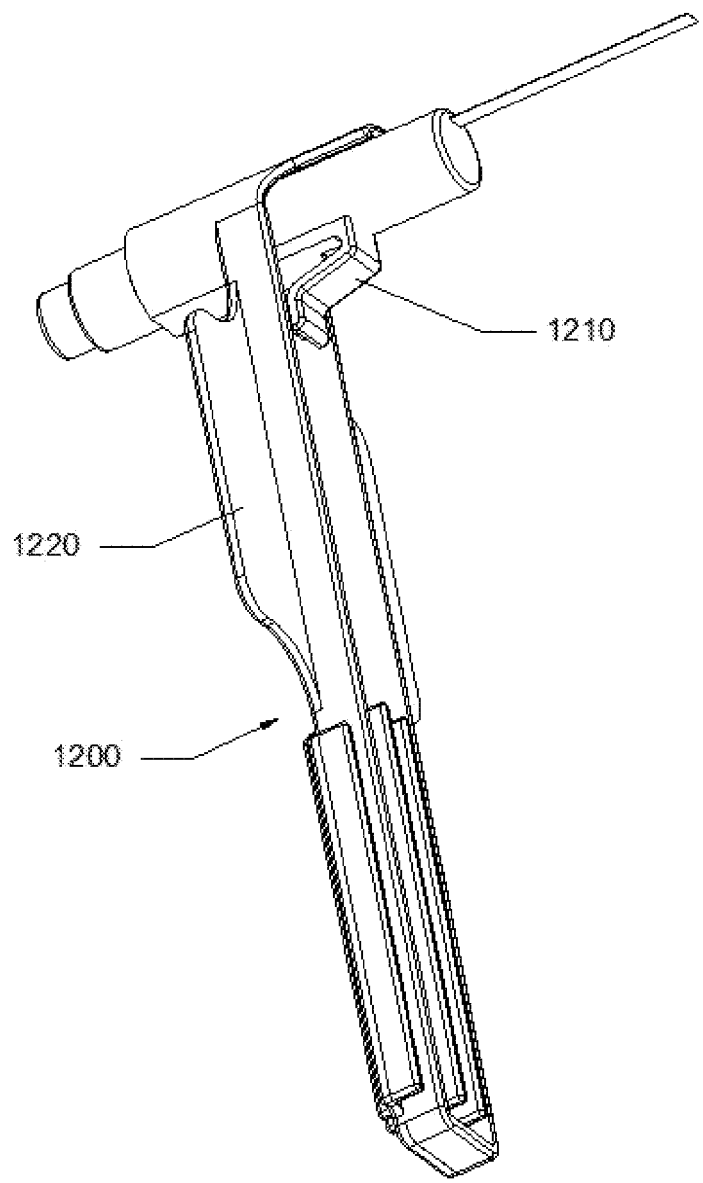
FIG. 12 illustrates a holder for use with a force sensing device, in accordance with an embodiment of the present disclosure.

FIG. 12 illustrates a holder 1200 for use with a force sensing device, in accordance with an embodiment of the present disclosure. Holder 1200 may be added to force sensing device 800, for example, if none of the body surfaces that are anticipated to form a shelf with registration plate 840 are available. Holder 1200 includes a mechanical lock 1210 and a chin paddle 1220. Chin paddle 1220 serves as an alternate to the registration plate. Thus, chin paddle 1220 is an alternate means of registering a patient to the force sensing device. Holder 1200 may also be adjusted to slide along tube 830 of force sensing device 800. Holder 1200 may be detachable or permanently built into any force sensing device, described herein.

Figure 13:
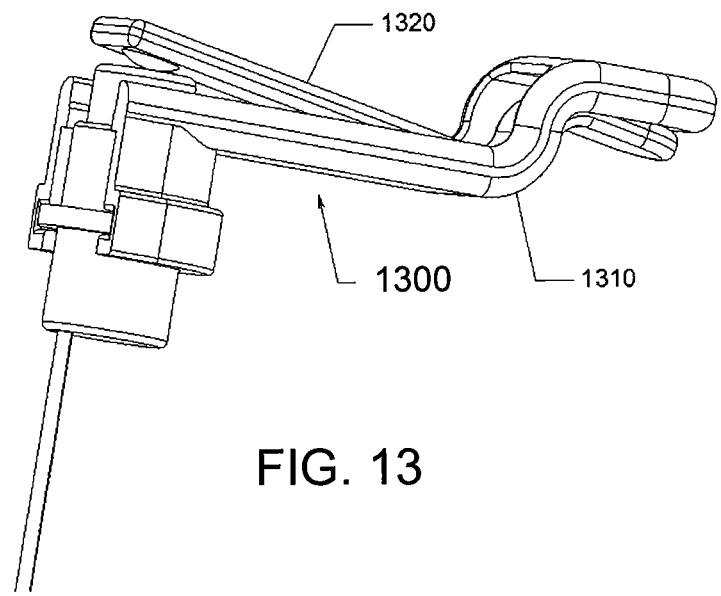
FIG. 13 illustrates an offset attachment for use with a force sensing device, in accordance with an embodiment of the present disclosure.

FIG. 13 illustrates an offset attachment for use with a force sensing device, in accordance with an embodiment of the present disclosure. Offset attachment 1300 attaches to, for example, registration plate 840. Offset attachment 1300 may be detachable or permanently built into a force sensing device, described herein. Offset attachment 1300 provides access to additional body force measurement locations that would not otherwise be easily accessible. Offset attachment 1300 includes registration plate extension 1310, and an activator extension 1320. Registration plate extension 1310 provides additional surface area to lie flat against the roof of a patient's mouth and provide a registration point. Activator extension 1320, similarly, provides additional surface area to receive compressive force from a body part of interest that would subsequently be applied to cap 810. Additionally, although not shown, a mechanical lock may be added to offset attachment 1300.

Figure 14:
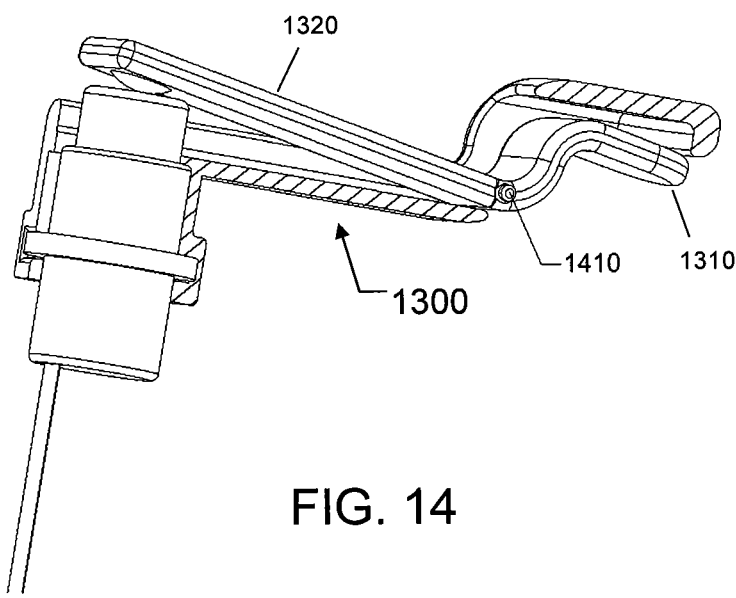
FIG. 14 illustrates a sectional view of a registration plate extension of the offset attachment shown in FIG. 13, in accordance with an embodiment of the present disclosure.

FIG. 14 illustrates a sectional view of a registration plate extension of the offset attachment shown in FIG. 13, in accordance with an embodiment of the present disclosure. This sectional view of registration plate extension 1310 shows an activator extension pivot 1410, which allows activator extension 1320 to move pivotably with respect to registration plate extension 1310. As a result, angular, as well as linear displacements and variations, may be incorporated for measurement based on the use of an appropriate offset attachment. Although specifically shown in use with force sensing device 1000, offset attachment 1300 as shown in FIGS. 13 and 14 may be adapted for use with other embodiments of force sensing devices and additional components such as holders, described herein.

Figure 15A:
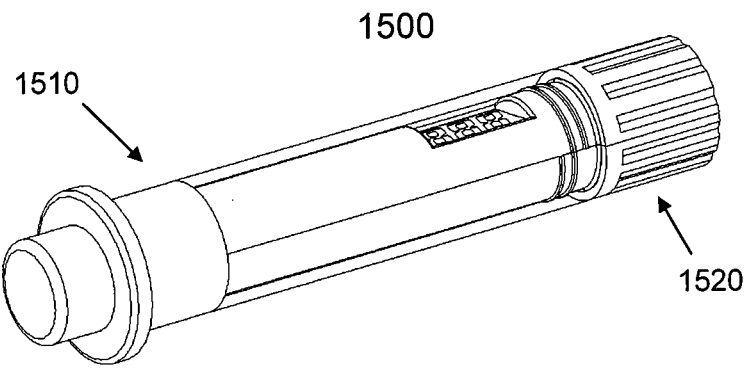
FIG. 15A illustrates a force sensing device with a self-contained assembly, in accordance with an embodiment of the present disclosure.

FIG. 15A illustrates a force sensing device with a self-contained assembly, in accordance with an embodiment of the present disclosure. Force sensing device 1500 includes a disposable tip 1510, and a self contained enclosure 1520. Disposable tip 1510 securely engages with enclosure 1520 using threads or similar mechanical engagements. Disposable tip 1510 may be a mechanical assembly or could also be a slip-on or roll-on sheath.

Figure 15B:
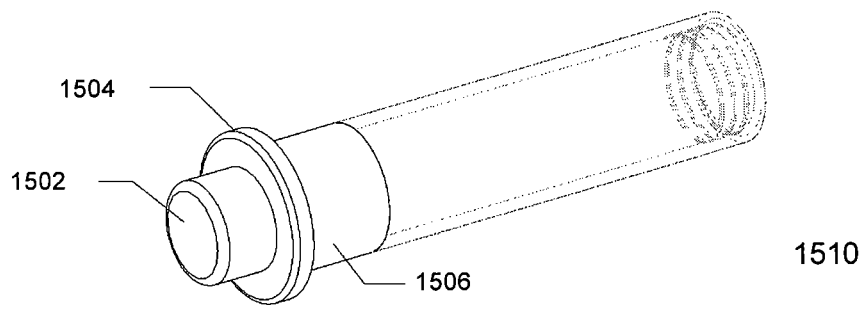
FIG. 15B illustrates a view of disposable tip of the force sensing device, in accordance with an embodiment of the present disclosure.

FIG. 15B illustrates a view of disposable tip 1510 of the force sensing device, in accordance with an embodiment of the present disclosure. Disposable tip 1510 includes cap 1502, registration plate 1504, barrel 1506, and disposable tip extension 1520. A portion of disposable tip 1510 is shown as being made of a translucent material in FIG. 15B. Disposable tip 1510 may be, for example, a disposable and removable sheath.

Figure 15C:
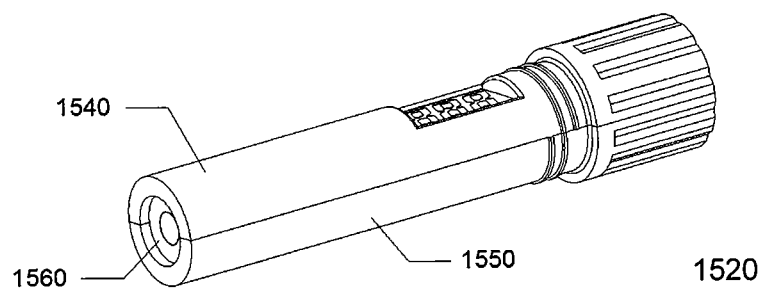
FIG. 15C illustrates self-contained enclosure 1520 of the force sensing device, in accordance with an embodiment of the present disclosure.

FIG. 15C illustrates self-contained enclosure 1520 of the force sensing device, in accordance with an embodiment of the present disclosure. More specifically, FIG. 15C illustrates enclosure 1520 without disposable tip 1510. Enclosure 1520 includes two components. A first and second top enclosure 1540 and 1550 are shown. Also shown is a pusher 1560 that interacts to receive a compressive force from cap 1502.

Figure 16:
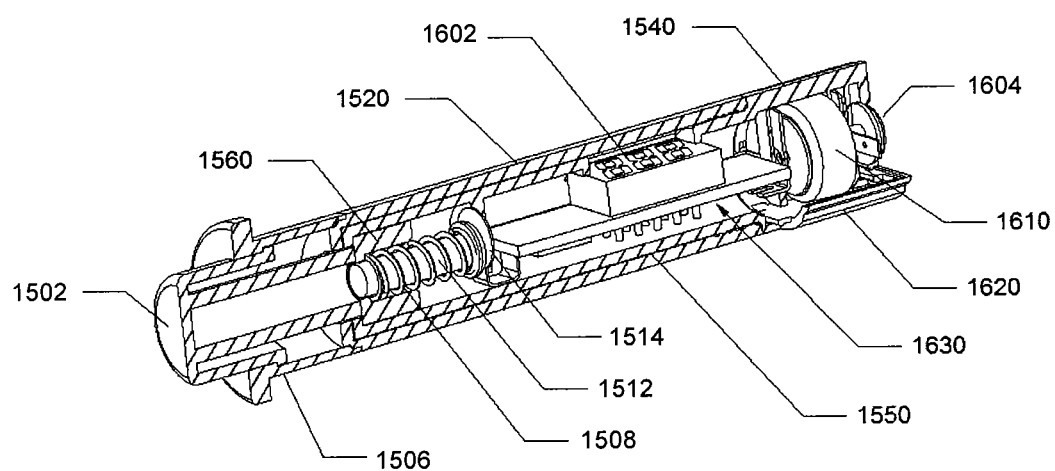
FIG. 16 illustrates a cross sectional view of all of the components of the force sensing device shown in FIGS. 15A, 15B, and 15C, in accordance with an embodiment of the present disclosure.

FIG. 16 illustrates a cross sectional view of all of the components of the force sensing device shown in FIGS. 15A, 15B, and 15C, in accordance with an embodiment of the present disclosure. Cap 1502 move slidably within barrel 1506 when cap 1502 receives a compressive force from a body part such as a tongue. Cap 1502 pushes against pusher 1560, causing pusher 1560 to move slidably within self-contained enclosure 1520. The movement of pusher 1560 exerts a force against compressive element 1508. The force exerted against compressive element 1508 causes compressive element 1508 to compress and press against sensor contact 1512, which then causes a force exerted against force sensing element 1514. The transfer of forces is complete when force sensing element 1514 transfers data indicative of the compressive force applied from the body part to printed circuit assembly 1630. Printed circuit assembly 1630 processes the data indicative of the compressive force and outputs data to be displayed by display mechanism 1602. A battery 1610 for powering printed circuit assembly 1630 is accessibly by a removable battery door 1620. A reset switch 1604 sends an instruction to printed circuit assembly 1630 to instruct display mechanism 1602 to reset its display. An operating mode switch (not shown) may also be attached to printed circuit assembly 1630.

Alternatively, compressive element 1508 may be optional. Thus, the force sensing device described with respect to FIG. 16 may operate without compressive element 1508. Instead, the movement of pusher 1560 exerts a force against sensor contact 1512, which causes a force exerted against force sensing element 1514. Additionally, pusher 1560 and sensor contact 1512 may be combined into a single component which may cause any force applied to the cap to be directly transmitted to force sensing element 1514.

Figure 17:
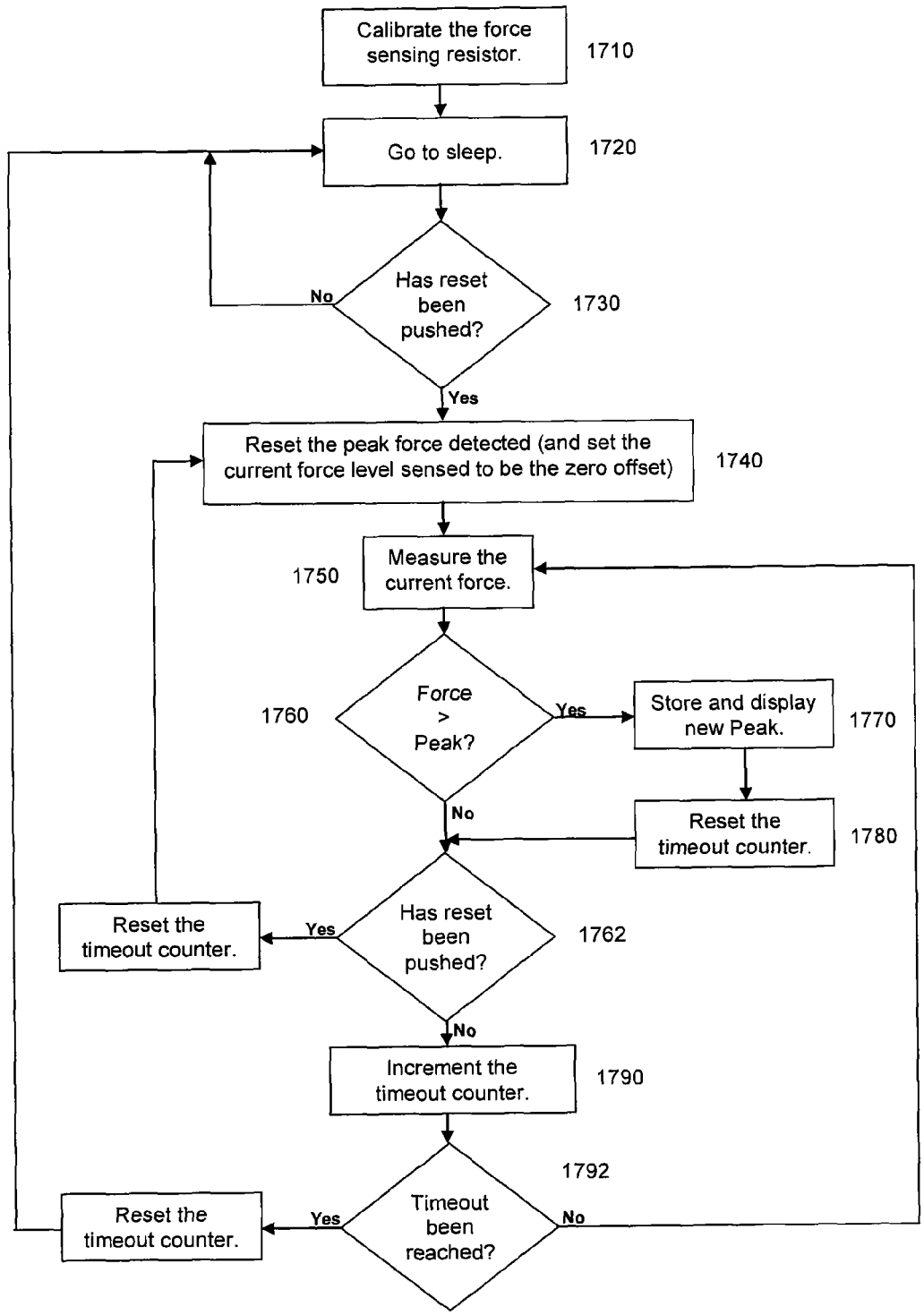
FIG. 17 illustrates a flow diagram for a force sensing device, in accordance with an embodiment of the present disclosure.

FIG. 17 illustrates a flow diagram for a force sensing device, in accordance with an embodiment of the present disclosure. At step 1710, force sensing element 1514 is calibrated. Specifically, as force sensing element 1514 may be a force sensing resistor, either a single point or multi-point calibration may be utilized.

At step 1720, a force sensing device will go into a sleep mode to conserve battery power.

At decision block 1730, a force sensing device determines if reset switch 1604 has been activated. If reset switch 1604 has been activated, the method proceeds to step 1740.

At step 1740, in response to activation of reset switch 1604, any current peak force level displayed by display mechanism 1602 is cleared. Any current force level sensed could optionally be set as the zero offset level from which all subsequent force measurements would be taken.

At step 1750, the force sensing device may continuously monitor and measure a current force, and display the maximum peak force observed until either the device times out or the reset switch is once again activated.

At decision block 1760, if the measured force is greater than the maximum peak force, the method continues to step 1770 where the measured force is stored and displayed as the new peak force. Then the method proceeds to step 1780 to reset a timeout counter.

If the measured force is not greater than the maximum peak force, the method proceeds to another decision block 1762 to determine if the reset switch has been activated. If yes, then the method resets the timeout counter and returns to step 1740. If no, then the method proceeds to step 1790 to increment the timeout counter.

At decision block 1792, if a timeout has been reached, the timeout counter is reset and the device returns to step 1720 to go into sleep mode. If a timeout session has not been reached, the method proceeds back to step 1750 to measure the force. Thus, once force detection apparatus 1500 is awake, it will continuously monitor and display a maximum peak force observed until either a timeout condition is reached or reset switch 1604 is activated.

Figure 18:
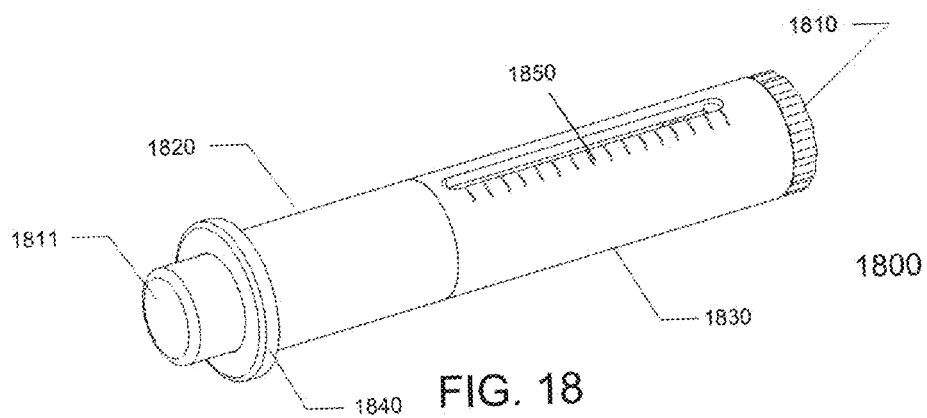
FIG. 18 illustrates a force sensing device in accordance with an embodiment of the present disclosure.

FIG. 18 illustrates a force sensing device in accordance with an embodiment of the present disclosure. Force sensing device 1800 includes a cap 1810, barrel 1820, tube 1830, and resistance adjuster 1810. Also included are registration plate 1840 and resistance scale 1850. Resistance adjuster 1810 is utilized to change the resistance of a compressive resistance element within tube 1830. The change in resistance is shown on resistance scale 1850, which displays the current resistance given by the compressive resistance element. Usage of force sensing device 1800 is similar to other embodiments of a force sensing device described above.

Figure 19A:
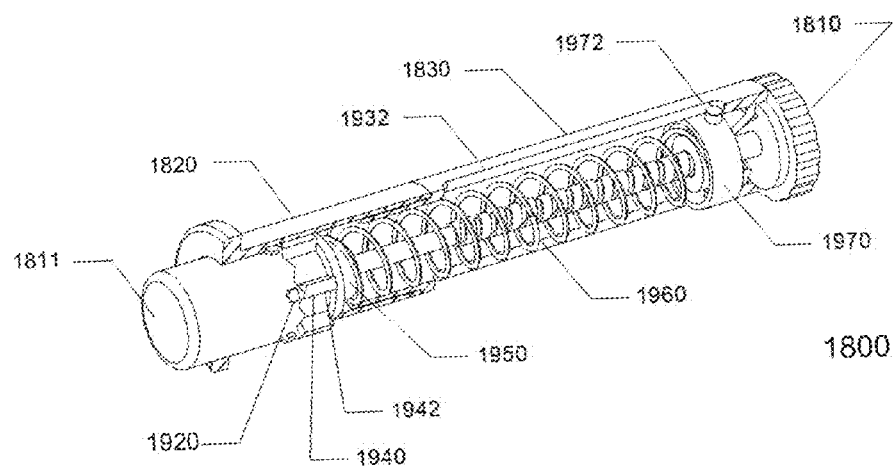
FIGS. 19A and 19B illustrates components associated with creating an auditory and tactile indication that a tongue's force has satisfied a resistance of resistance element, in accordance with an element of the present disclosure.
Figure 19B:
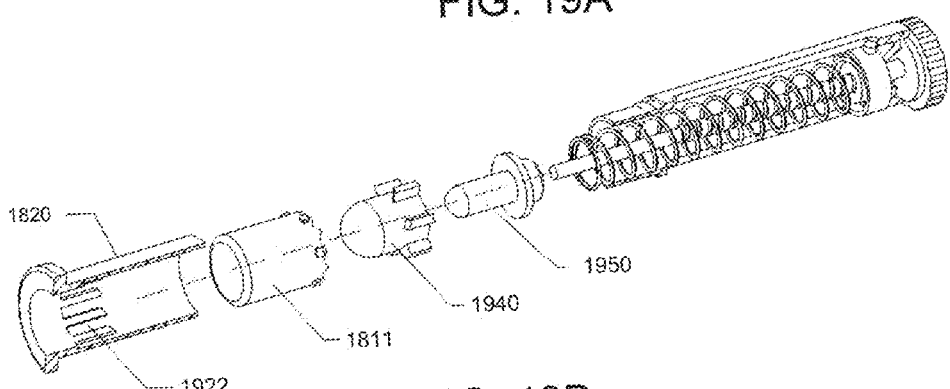

FIG. 19A illustrates the internal components of force sensing device 1800 shown in FIG. 18, in accordance with an embodiment of the present disclosure. FIG. 19B also illustrates internal components of force sensing device 1800, in accordance with an embodiment of the present disclosure.

Compressive element 1960 is shown along with resistance stop 1970. Compressive element 1960 is adjustable by resistance adjuster 1810 and resistance stop 1970 serves as a means to stop compressive element 1960 from moving past a certain point.

Tube 1830 also includes tube-anti rotation element 1932. Resistance stop 1970 also includes an anti-rotation element 1972. These anti-rotation elements 1932 and 1972 assist in translating rotational motion of resistance adjuster 1810 into exercise resistance supplied by compressive element. Anti-rotation elements 1932 and 1972 work in combination to prevent resistance stop 1710 from rotating such that when resistance adjuster 1810 is turned, the resistance stop 1970 is threaded forward or backwards to precompress the spring.

Resistance adjuster 1810 includes a threaded rod. The function of the threaded rod of resistance adjuster 1810, in combination with resistance stop 1970 and anti-rotation elements 1932 and 1970 may be replaced by a mechanical slide with mechanical lock in order to have compressive element 1960 locked at one particular resistance and provide an even fixed resistance for the force sensing device 1800. Resistance adjuster 1810 effectively sets the exercise resistance that a patient feels when pushing against cap 1810. Usage of the threaded rod is advantageous because exercise resistance may be continuously adjusted over a range of available exercise resistances to provide a force sensing device that is customizable and adjustable for different patients and different resistances.

FIGS. 19A and 19B illustrates components associated with creating an auditory indication that a tongue's force has satisfied a resistance of compressive element 1960, in accordance with an element of the present disclosure. Specifically, these components cause a mechanical "click" once cap 1811 has traveled a predetermined distance. For example, a "click" is heard when cap 1811 travels 0.25 inches. The components are cap 1811, barrel 1820, tube 1830, a plunger 1940, a resistance hub 1950, and resistance element 1960. Cap 1811 includes a cap alignment boss 1920, barrel 1820 includes a barrel "click" channel 1922, and plunger 1940 includes a plunger rail 1942. Compressive element 1960 may be either set at a fixed resistance or be adjustable.

Cap 1811 moves slidably within barrel 1820, whose rotational orientation is constrained by barrel "click" channel 1922. Based on a force supplied by a user's tongue to cap 1811, cap 1811 pushes against plunger 1940 both axially and rotationally. Cap 1811 may have a crown-like structure which facilitates force to be directed rotationally. Barrel "click" channel 1922 may be designed such that one side may be longer than the other. Thus, once plunger 1940 is pushed beyond the long side of barrel "click" channel 1922, plunger 1940 experiences a rotation because it is no longer rotationally constrained and then plunger 1940 rotates toward an adjacent barrel "click" channel 1922. This causes a "click" or an audible indication.

Each time a "click" is produced, plunger 1940 rotates. Resistance hub 1950 allows plunger 1940 to rotate freely without causing a twisting force to be experienced by compressive element 1960.

Operationally, a user receives both auditory and tactile feedback each time an exercise or measurement objective is completed. All embodiments described herein provide additional options for evaluating tongue fatigue of patients. The additional options include assessing the ability to repeatedly exert a body force in order to achieve an exercise objective and counting either the number of times the individual achieved the objective within a fixed time interval or the elapsed time it takes an individual to achieve the objective a fixed number of times.

Figure 20:
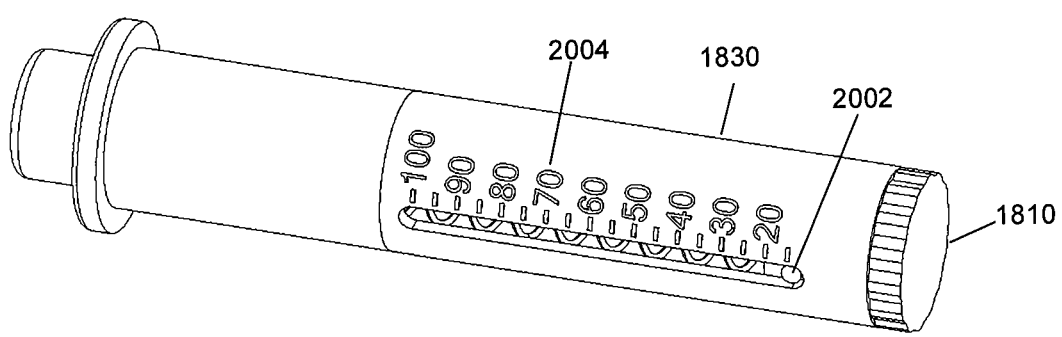
FIG. 20 illustrates a measurement scale to be used with the embodiments described within, in accordance with an embodiment of the present disclosure.

FIG. 20 illustrates a measurement scale to be used with the embodiments described within, in accordance with an embodiment of the present disclosure. Measurement scale 2004 may reside on the surface of tube 1830, and have an indicator 2002 that moves corresponding to adjustment of resistance adjuster 1810. Measurement scale 2004 includes tick marks, each representing a percentage of peak force. For example "100" in measurement scale 2004 may represent a nominal/average peak force setting that a particular population (e.g. adult males, healthy elderly person, child, etc.) may achieve. In other words, as resistance adjuster 1810 is adjusted to adjust compressive element 1960, indicator 2002 moves to an appropriate position on measurement scale 2004 to indicate a level of resistance representing the current resistance of compressive element 1960. Other values on measurement scale 2004 may represent a certain percentage of the nominal/average peak force associated with the "100" setting. A "37" may represent a setting of 37% of the nominal/average peak force that an adult male can achieve. Thus, immediate feedback may be provided to a clinician or therapist of what type of force may be exerted by a patient's tongue relative to a given population sample, when the embodiments described herein including a measurement scale are used.

Figure 21:
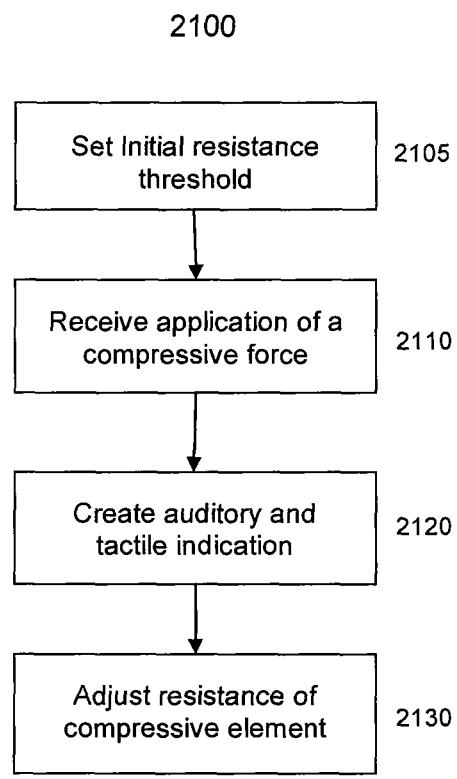
FIG. 21 illustrates an exemplary method for measuring tongue force, in accordance with an embodiment of the present disclosure.

FIG. 21 illustrates an exemplary method 2100 for measuring tongue force, in accordance with an embodiment of the present disclosure. At step 2105, a resistance threshold is adjusted. The resistance threshold is set based on a predetermined scale associated with a nominal resistance value achievable by a particular population. For example, a scale level of 100 is equivalent to 100 percent of the nominal resistance value. The resistance threshold represents a resistance suitable for user tongue exercises.

At step 2110, at least one application of compressive force from a user's tongue is received by the cap of a force sensing device. The cap moves slidably relative to an enclosure, against a resistance of a compressive element, in response to receiving an application of compressive force.

At step 2120, an auditory and tactile indication is created for the user in response to each instance that an application of compressive force satisfies a resistance threshold.

The foregoing Detailed Description is to be understood as being in every respect illustrative and exemplary, but not restrictive, and the scope of the disclosure is not to be determined from the Detailed Description, but rather from the claims as interpreted according to the full breadth permitted by the patent laws. It is to be understood that the embodiments shown and described herein are only illustrative of the principles of the present disclosure and that various modifications may be implemented by those skilled in the art without departing from the scope and spirit of the present disclosure.

We claim:

1. A force sensing device, comprising:
  a force sensing element; and
  an intraoral registration plate for supporting the force sensing element, the intraoral registration plate comprising a single surface configured to form a shelf against an interior surface of a user's upper teeth and an interior surface of the user's lower teeth to maintain a position of the force sensing element relative to a force exerted by the user's tongue.

2. The force sensing device of claim 1, wherein the intraoral registration plate maintains a fixed position from which force measurements are taken.

3. The force sensing device of claim 1, further comprising:
a longitudinal element having two ends, a first end coupled perpendicularly to the intraoral registration plate.

4. The force sensing device of claim 1, further comprising: measurement equipment attached to the force sensing element, wherein the measurement equipment comprises:
a processor that receives data from the force sensing element;
a display that displays the data; and
a reset actuator.

5. The force sensing device of claim 1, wherein the force sensing element is a conductive sensor.

6. The force sensing device of claim 1, further comprising:
an enclosure housing the force sensing element; and
a cap slidably disposed within the enclosure and engaged to contact with the force sensing element such that the cap pushes against the force sensing element axially in response to the user's tongue applying compressive force to the cap.

7. TTTTTT The force sensing device of claim 6, further comprising:
a circuit assembly, disposed within the enclosure, configured to receive data representative of a sensed compressive force from the force sensing element; and
a display disposed on the enclosure, that displays the sensed compressive force based on the data representative of the sensed compressive force received by the circuit assembly.

8. The force sensing device of claim 1, further comprising:
an enclosure housing the force sensing element; and
a compressive element, coupled to the force sensing element, within the enclosure; and
a cap slidably disposed within the enclosure and engaged to contact with the compressive element such that the cap is configured to push against the compressive element axially in response to the user's tongue applying compressive force to the cap.

9. The force sensing device of claim 8, wherein the cap is configured to create an auditory and tactile indication to the user in response to the cap moving linearly within the enclosure.

10. The force sensing device of claim 8, further comprising:
a resistance adjuster, coupled to the compressive element, configured to adjust the compressive element in order to change a resistance of the compressive element.

11. The force sensing device of claim 1, wherein the force sensing element is a pneumatic element.

12. A method for measuring tongue force using a tongue force measurement device having an enclosure, a compressive element and a cap, the method comprising:
receiving at least one application of compressive force from a user's tongue at the cap of the tongue force measurement device, wherein the cap moves slidably relative to the enclosure, against a resistance of the compressive element, in response to receiving an application of compressive force;
creating an auditory and tactile indication of the cap for the user in response to each instance that an application of compressive force satisfies a resistance threshold by the cap moving slidably a predetermined distance against the compressive element.

13. The method of claim 12, wherein the tongue force measurement device is further configured to allow the resistance threshold of the compressive element to be adjusted and further comprising:
receiving at least one application of adjustment of the resistance threshold for the compressive element.

14. The method of claim 13, wherein receiving at least one application of adjustment of the resistance threshold comprises:
setting the resistance threshold based on a predetermined scale associated with a nominal resistance value achievable by a particular population.

15. The method of claim 14, wherein scale level of 100 is equivalent to 100 percent of the nominal resistance value.

16. The method of claim 13, wherein at least one application of adjustment of the resistance threshold comprises:
adjusting the resistance threshold continuously over a range of interest.

17. A force sensing device, comprising:
an enclosure;
a compressive element within the enclosure; and
a cap slidably disposed within the enclosure and engaged to contact with the compressive element such that the cap is configured to push against the compressive element axially in response to a tongue applying compressive force to the cap and to create an auditory and tactile indication to a user in response to the cap moving axially a predetermined distance.

18. The force sensing device of claim 17, further comprising:
a registration plate integral with the enclosure, that forms a shelf against a body part to maintain a position of the enclosure relative to the tongue to facilitate the cap moving slidably during use.

19. The force sensing device of claim 18, wherein the registration plate maintains a fixed position from which force measurements are taken.

20. The force sensing device of claim 17, wherein the compressive element comprises a spring.

21. The force sensing device of claim 17, wherein the force sensing device is covered by a disposable sheath.

22. The force sensing device of claim 17, further comprising:
a resistance adjuster, coupled to the compressive element, configured to adjust the compressive element in order to change a resistance of the compressive element.

23. The force sensing device of claim 17, further comprising:
a resistance scale integrated with the enclosure, to display a current resistance provided by the compressive element.

24. The force sensing device of claim 23, wherein the resistance scale represents a predetermined scale associated with a nominal resistance value achievable by a particular population.

25. The force sensing device of claim 17, wherein the predetermined distance is 0.25 inches.

26. A force sensing device, comprising:
an enclosure;
a force sensing element within the enclosure;
a registration plate integral with the enclosure and configured to form a shelf against an interior surface of a user's upper teeth and an interior surface of the user's lower teeth; and
a cap slidably disposed within the enclosure and engaged to contact with the force sensing element such that the cap is configured to push against the force sensing element in response to a tongue applying compressive force to the cap.

27. The force sensing device of claim 26, wherein the registration plate is configured to maintain a fixed position from which force measurements are taken.

\* \* \* \* \*